July 29, 1975 K. F. FESSLER Plant Pat. 3,752
AZALEA PLANT
Filed July 2, 1974
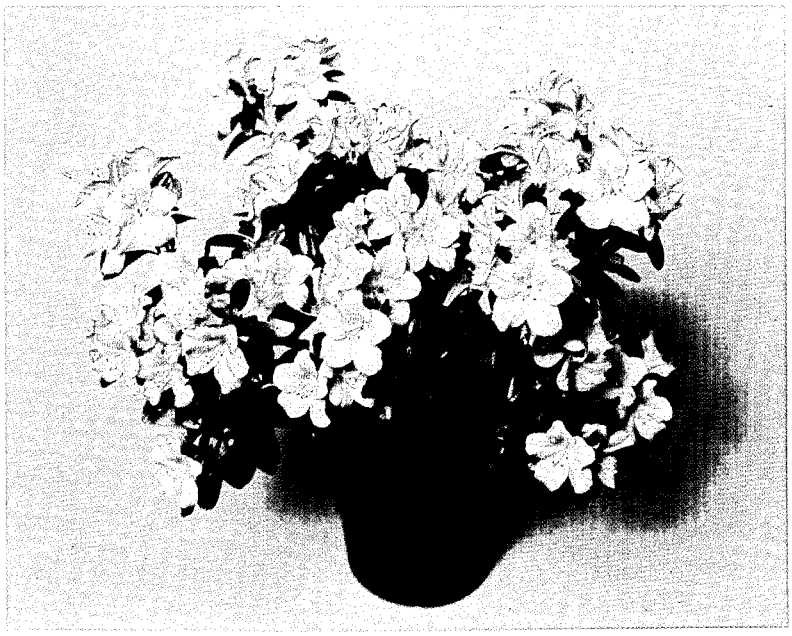
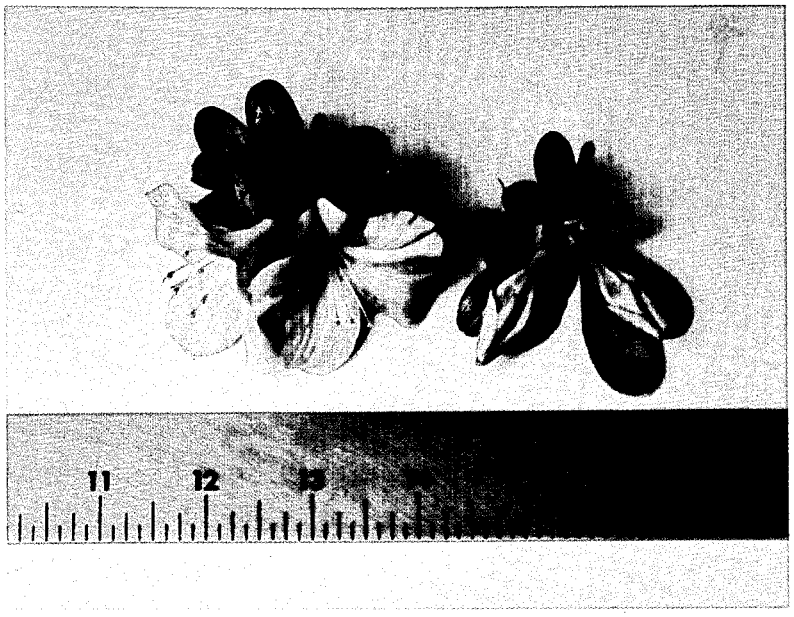

United States Patent

Plant Pat. 3,752

Patented July 29, 1975

3,752

AZALEA PLANT

Kenneth Frank Fessler, Woodburn, Oreg., assignor to Geo. J. Ball, Inc., West Chicago, Ill.

Filed July 2, 1974, Ser. No. 485,095

Int. Cl. A01h *5/00*

U.S. Cl. Plt.—56 1 Claim

ABSTRACT OF THE DISCLOSURE

A new hybrid azalea variety distinguished by its profuse production of single flowers of medium size, having a pink color resembling that of Dorothy Gish (Plant Pat. 146) and being particularly suitable for pot forcing on a year around production basis.

BACKGROUND OF THE NEW PLANT

This new variety of azalea was discovered by me in April 1971 at Woodburn, Oreg., as a sport of Dogwood (Plant Pat. 3,093), which is being propagated by me at Woodburn, Oreg., for the commercial trade. The unusual coloration of the flowers of this sport, appearing on the white flowered Dogwood, and the fact that its flowers are single resulted in my selecting this sport for propagation and test. Asexual propagation of this sport, by cuttings, under my direction at Woodburn, Oreg., through successive generations, has shown that, although retaining the advantageous characteristics of the parent Dogwood, the coloration and the single flower distinction of this new azalea variety hold true from generation to generation and appear to be firmly fixed. Propagation of this new plant by cuttings is now being carried on at both Woodburn and Salem, Oreg.

DESCRIPTION OF THE DRAWING

My new variety of azalea plant is illustrated by the accompanying photographic drawing in which the upper view shows the potted plant in full bloom and the lower view shows specimens of buds, flowers and foliage in more detail, the color rendition of the drawings being as nearly true as it is reasonably possible to be had through conventional photographic procedures. The lower view and swatch show actual bloom colors.

DESCRIPTION OF THE NEW PLANT

The following is a detailed description of my new azalea plant with color designations according to the Robert F. Wilson Horticultural Colour Chart published by the Royal Horticultural Society of London, England, in collaboration with the British Colour Council.

The plant

Origin: Sport.
Parentage: Dogwood (Plant Pat. 3,093).
Classification:
*Botanic.*—Rhododendron.
*Commercial.*—Hybrid azalea.
Form: Spreading bush for pot culture.
Height: Medium.
Growth: Vigorous, sturdy, upright and well branched.
Foliage: Abundant.
*Leaf.*—Shape: Oblanceolate to spatulate with a mucronate apex consisting of a tiny white point 1/32 inch long. Texture: Hirsute. Aspect: Glossy. Color: upper side—Parsley Green 00962. Under side—Spinach Green 0960/3. Ribs and veins: Alternate pinnate venation.

The bud

Size: 1 to 1¼ inch long; ¼ to ½ inch in diameter.

Shape: Obanceolate, long and pointed.
Opening: The bud opens slowly.
Color:
*When sepals first divide.*—Cardinal Red 822/2.
*When sepals unfurl.*—Rose Opal 022.
Sepals: Upstanding.
*Color.*—Inside—Agathia Green 60/2. Outside—Agathia Green 60/2.
Calyx: Funnel-shaped and deeply cleft.
*Size.*—Small. Aspect: Hairy.
*Splitting.*—Calyx splits.
Peduncle: Erect and ¼ inch long.
*Hairs.*—Peduncle is hairy and amount of hairs varies with the length of the stem.
*Color.*—Pod Green 061 with hairs of Garnet Brown 00918/3.

The flower

Blooming habit: Recurrent. The plant blooms profusely, normally once in early to midseason of spring, and has a tendency to produce a few blooms in the fall.
Size of flower: Medium, 2¼ to 2½ inches in diameter and 1¼ to 1½ inches in depth.
Borne: As single flowers 4 to 7 on a stem.
Shape: Funnel-shape. The petals recurve as the flower matures.
Petalage: Usually 5 petals.
*Form.*—Spatulate.
*Arrangement.*—Petals are fused at the base to form a funnel-shape flower.
*Color.*—Face side—Delft Rose 020/1 shading to 020 at edges; blotched with China Rose 024/1 and freckled with 024 at base of standard and upper wings. Reserve side—Claret Rose 021/1.
*Texture.*—The petals are extraordinarily thick.
*Aspect.*—Satiny.
*Petaloids.*—Occasionally one. Color: Same as petals.
Peduncle: Erect and hairy. ¼ inch long.
*Color.*—Pod Green 061.
Fragrance: None.
Discoloration after full bloom: Empire Rose 0621.
Effect of weather: None.
Persistence: Petals drop when blossom dries.
Lasting quality: Very good.

Reproductive organs

Stamens:
*Anthers.*—5 to 7 in number, 1/16 inch long. Arrangement—Encircling the pistil.
*Filaments.*—As long or longer than the height of the corolla. Color: Rose Opal 022/1.
*Pollen.*—Color—Primrose Yellow 601/3.
Pistils: Number—One. Extends above the anthers.
*Stigma.*—Color—Carmine 21/1.
Ovaries: Superior.

The plant form and shape of this new variety of azalea plant resembles the variety Dogwood (Plant Pat. 3,093). In color, however, the flowers of this new plant most nearly resembles that of Dorothy Gish (Plant Pat. 146) and it is mainly in this respect that it deffers from its parent. The single flowers of the new plant also provide an attractive display of the flower color because of the spreading or wide open petal arrangement.

The claim:

1. The new and distinct variety of azalea plant substantially as herein shown and described, characterized by being a sport of Dogwood (Plant Pat. 3,093), similar to its parent in form, shape and growth habit but being distinguished by the bright pink color of its blossoms.

No references cited.

ROBERT E. BAGWILL, Primary Examiner